United States Patent [19]

Shue

[11] Patent Number: 4,878,501

[45] Date of Patent: * Nov. 7, 1989

[54] ELECTRONIC STETHOSCOPIC APPARATUS

[76] Inventor: Ming-Jeng Shue, No. 14, Lane 8, Chung-I St., Taichung, Taiwan

[*] Notice: The portion of the term of this patent subsequent to Feb. 9, 2005 has been disclaimed.

[21] Appl. No.: 66,222

[22] Filed: Jun. 25, 1987

Related U.S. Application Data

[63] Continuation-in-part of Ser. No. 27,101, Mar. 13, 1987, and a continuation-in-part of Ser. No. 926,578, Nov. 4, 1986, Pat. No. 4,723,555.

[51] Int. Cl.⁴ .............................................. A61B 5/02
[52] U.S. Cl. .................................. 128/715; 128/680; 128/773
[58] Field of Search ............... 128/701, 715, 773, 904, 128/680; 381/67, 100, 123

[56] References Cited

U.S. PATENT DOCUMENTS

| | | | |
|---|---|---|---|
| 2,755,336 | 7/1956 | Zener et al. ........................... | 381/67 |
| 3,110,770 | 11/1963 | Howell ................................... | 381/67 |
| 3,160,708 | 12/1964 | Andries et al. ........................ | 381/67 |
| 3,247,324 | 4/1966 | Cefaly et al. .......................... | 381/67 |
| 3,989,895 | 11/1976 | O'Daniel, Sr. ....................... | 128/715 |
| 4,048,444 | 9/1977 | Giampapa ............................. | 381/67 |
| 4,071,694 | 1/1978 | Pfeiffer ................................. | 381/67 |
| 4,072,822 | 2/1978 | Yamada ................................. | 381/67 |
| 4,170,717 | 10/1979 | Walshe ................................. | 381/67 |
| 4,248,241 | 2/1981 | Tacchi ................................. | 128/715 |
| 4,254,302 | 3/1981 | Walshe ................................. | 381/67 |
| 4,301,809 | 11/1981 | Pinchak .............................. | 128/715 |
| 4,362,164 | 12/1982 | Little et al. ......................... | 128/715 |
| 4,377,727 | 3/1983 | Schwalbach ........................ | 128/715 |
| 4,438,772 | 3/1984 | Slavin ................................. | 128/715 |
| 4,458,693 | 7/1984 | Badzinski ............................ | 128/715 |
| 4,498,188 | 2/1985 | Hofer ................................... | 128/715 |
| 4,534,058 | 8/1985 | Hower ................................. | 128/715 |
| 4,618,986 | 10/1986 | Hower ................................. | 128/715 |
| 4,619,268 | 10/1986 | Uphold ............................... | 128/715 |
| 4,672,976 | 6/1987 | Kroll ................................... | 128/715 |

Primary Examiner—Francis Jaworski
Assistant Examiner—George Manuel
Attorney, Agent, or Firm—Lee C. Robinson, Jr.

[57] ABSTRACT

An electronic stethoscopic apparatus including: a housing with a main body having a plurality of switches and jacks electrically installed therein; an audio-signal amplifying device incorporating a pre-amplifying circuit, a low pass filter and a volume controller disposed in the main body and electrically coupled with the switches and jacks; a battery supply replaceably provided in the main body and electrically connected to the audio-signal amplifying device; an audio-wave guiding device having transducers disposed therein for converting audio waves into electric signals and positioned on top of the main body and electrically connected to the audio-signal amplifying device; a wireless radio wave transmitting device also disposed in the main body to receive the electric signals and transmit the same as radio signals; an upper cover of the housing device connected to the top end of the main body and to the audio-wave guiding device; and a body contact device communicatively connected to the audio-wave guiding device. The apparatus permits auscultation can be made through an earphone/speaker and/or recorder for accurate diagnosis, the besides, remote auscultation or bedside group teachings can be achieved by turning on the wireless radio wave transmitting device enabling the radio wave signals to be received by those at a remote place.

6 Claims, 7 Drawing Sheets

ELECTRONIC STETHOSCOPIC APPARATUS

This application is a continuation-in-part of my copending application, Ser. No. 27,101, filed Mar. 13, 1987. The latter is a continuation-in-part of my copending application, Ser. No. 926,578 filed Nov. 4, 1986.

BACKGROUND OF THE INVENTION

This invention relates to a stethoscopic apparatus designed for multiple auscultation and historical recording of a patient and also designed for clearly transmitting the detected sound from the body portion of a patient.

A stethoscope is an indispensable medical instrument for detecting the sound of a body portion such as heart, lung, trachea, blood vessels, intestine, fetal heart, pulse beat, etc., so as to diagnose the illness of patients by doctors. The structure of the known stethoscope is usually composed of a chest piece with a diaphragm and a bell, a rubber tube connected to the chest piece at one end, and a pair of eartips arranged at another end of the rubber tube through a pair of flexible binaurals. This known stethoscope, though normally used by doctors, has the following problems:

(1) In order to allow the user to perform the auscultation without interference by external noise, the binaurals of the known stethoscope must be sufficiently resilient, which is uncomfortable for the user. If the resilience of the binaurals is reduced to a certain limit for user's comfort, the relay of the detected sound to the user's ear will be poorer than ever before.

(2) In addition to the above-noted defect, the sound detection of the known stethoscope is always made through the chest piece, which is positioned on the patient's body for obtaining the sound and effecting diagnosis. However, as the sound generated from the patient's body is usually very weak and also varies, and transformation of the detected sound is often caused by the known stethoscope, correct diagnosis cannot be made easily, and even erroneous diagnosis may be incurred from the transformed sound.

(3) Since the known stethoscopes are generally designed for a single user, it is very inconvenient if consultation and/or bed-side teaching is required for the same patient, particularly a female one, because the examination area is confined to a specific spot such as the heart, lung, etc., and observers need to perform the auscultation one after another on the specific spot for the same patient. Meanwhile, owing to a different time and different operation of each observer with different types of stethoscopes, various detected sounds may result in various diagnoses. Particularly, when a bed-side teaching has to be conducted, it is difficult to obtain unified diagnosis with the known stethoscopes.

(4) Since the known stethoscopes are normally designed to perform auscultation only on the spot, it is hard to make a diagnosis from a very weak and transient sound produced by the body portion of a patient, and, moreover, there is no recording function provided for the known stethoscopes to record the sound required for the patient's medical history for current diagnosis or for bed-side teaching purpose.

(5) It is sometimes necessary to transmit the sound produced by the body portions of a patient to a doctor who is located in a remote place for consultation purpose. However, unfortunately the conventional stethoscopic apparatus do not have proper means to achieve such mechanism.

In U.S. patent application entitled "Multi-Functional Radio/Wire Stethoscopic Apparatus" filed on Nov. 4, 1986 with Ser. No. 926,578 by the inventor of this application, there has been disclosed an improved stethoscopic apparatus which can be used to clearly detect the sound produced by the body portions of a patient and also to record the sound for the patient's history for correct diagnosis as well as for teaching purpose.

SUMMARY OF THE INVENTION

It is a primary object of this invention to provide a multi-functional electronic stethoscopic apparatus with which earphones can be used for performing auscultation without incurring uncomfort to the user's ear.

It is another object of this invention to provide a multi-functional electronic stethoscopic apparatus by which the sound of a patient's viscera can be sensitively detected and amplified for clear transmission to ensure correct diagnosis.

It is a further object of this invention to provide a multi-functional electronic stethoscopic apparatus by which several users can simultaneously perform auscultation for facilitating consultative diagnosis or for teaching purpose.

It is a still further object of this invention to provide a multi-functional electronic stethoscopic apparatus through which the diagnostic condition on the spot, such as the sound of a patient's viscera, the discussions held during consultation or bed-side teaching, etc., can be recorded for detailed study and later reference.

It is a still another object of this invention to provide a multi-functional electronic stethoscopic apparatus which includes a wireless radio wave transmitting device built therein for transmitting the sound produced by the body portions of the patient as a radio signal to be received by a receiver located at a remote place.

These and other objects of the present invention are achieved by providing a multi-functional electronic stethoscopic apparatus, which comprises: a housing device adapted for hand gripping and provided with an upper cover, a lower cover and a plurality of switches and jacks; an audio-signal amplifying device with input and output terminals disposed in the housing device preferably consisting of at least a pre-amplifying circuit means, a low pass filtering means and a power amplifier circuit means; an audio-wave guiding means disposed on the top end of the housing device with an upper portion thereof extending out of the upper cover; high sensitive transducing means arranged in an end portion of the audio-wave guiding means and electrically connected to the input of the audio signal amplifying device to convert the audio wave into an electric signal; a wireless radio wave transmitting device having a wireless radio wave generating circuit means, an antenna and a wireless radio on switch also disposed in the housing device to receive said electric signal and transmit the same as a wireless radio signal through the antenna; a battery supply replaceably installed in the housing device and electrically connected to the audio signal amplifying device and the wireless radio wave transmitting device through power switches of the housing device; and a body contact device with a sound wave duct connected to the upper portion of the audio-wave guiding means; thereby, during auscultation, an earphone or another sound outputting and/or recording device can be conveniently connected to the audio-signal amplifying device through the housing device for sound receiving, reproducing and recording operations. Besides, by the wireless radio wave transmitting device, remote auscultation and group bedside teaching of auscultation can be conveniently achieved through a rocketable receiver and an earphone.

Other salient features and advantages of the present invention will become clear from the following detailed description of preferred embodiments with reference to the accompanying drawings.

DETAILED DESCRIPTION OF THE PREFERRED EMBODIMENT

Referring to FIGS 1, 2, 3 and 4, the first preferred embodiment of an electronic stethoscopic apparatus according to this invention comprises: a housing unit 10 composed of a main body 11, an upper cover 12 with a through opening 121, and a lower cover 13; an audio-wave guide 30 having one end in engagement with the top of the main body 11 and a body contact device 40 fixedly connected to the audio-wave guide.

Figure 1:
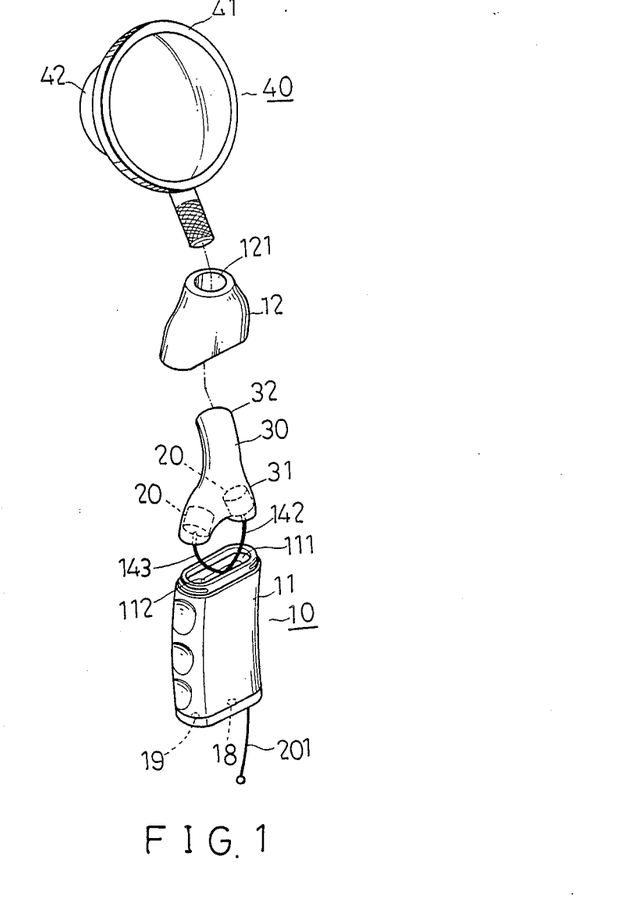
FIG. 1 is a an exploded and perspective view of a first preferred embodiment of an electronic stethoscopic apparatus according to this invention.
Figure 2:
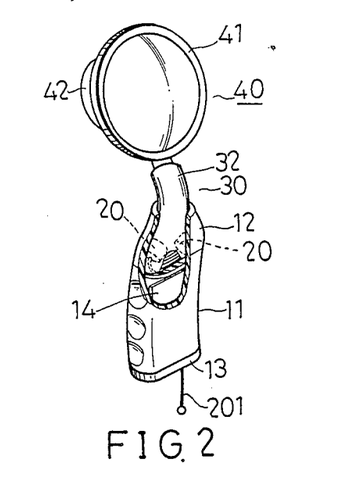
FIG. 2 is a perspective view showing the assembly, partly cut-off, of the first preferred embodiment of multi-functional stethoscopic apparatus in FIG. 1.
Figure 3:
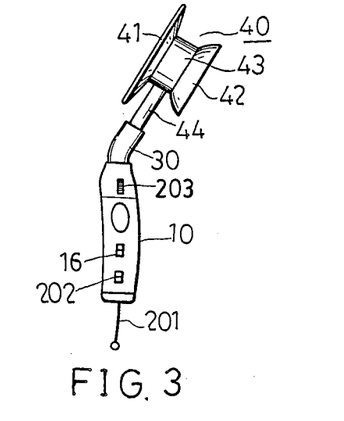
FIG. 3 is a side view of the assembled preferred embodiment of FIG. 1.
Figure 4:
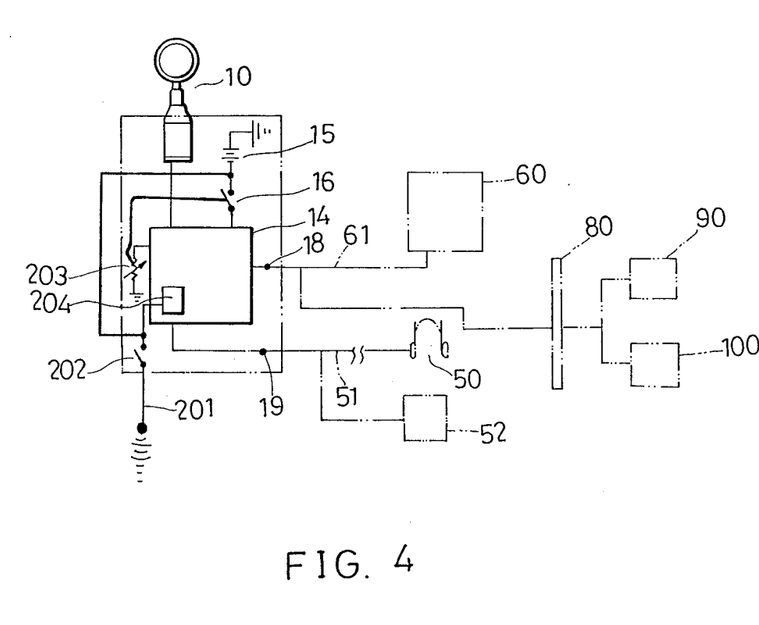
FIG. 4 is a block diagram illustrating the operational functions of the first preferred embodiment.
Figure 5:
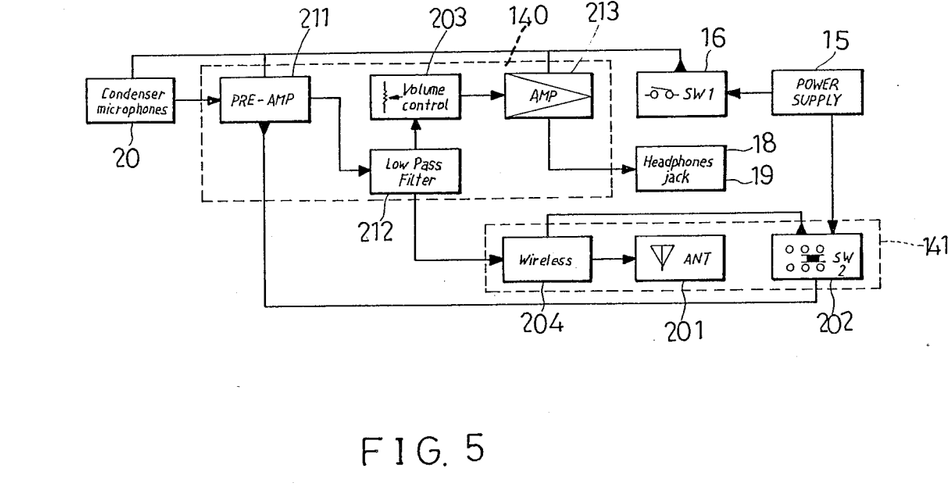
FIG. 5 is a functional block diagram of the audio wave signal amplifying device and the wireless radio wave transmitting device adopted in the electronic stethoscopic apparatus of the present invention.

As shown in FIGS. 2, 4 and 5, the main body 11, adapted for hand gripping, includes: PC board 14, having audio-signal amplifying device 140 and wireless radio wave transmitting device 141 formed thereon with a plurality of input and output terminals installed in the main body 11; a battery supply 15 provided in the main body 11 (batteries can be easily placed and replaced through the lower cover 13) and electrically connected to the audio-signal amplifying device 140 and wireless radio wave transmitting device 141 through power switch 16 and wireless radio on switch 202 respectively installed in a side wall of the main body 11, as shown in FIG. 3; a control knob 203, which is electrically coupled with the audio-signal amplifying device 140, provided at an upper side of the main body 11 for controlling signal output magnitude of the audio-signal amplifying device 140; a recorder jack 18 and an earphone/speaker jack 19 respectively provided in the lower end of the main body 11 and electrically connected to the output terminals of the audio-signal amplifying device 140 and a level surface 111 with a central recess 112 formed on top of the main body 11, as shown in FIG. 1.

The audio-wave guide 30, formed in a hollow Y-shape and made of flexible material, includes a lower forked portion 31, having a pair of microphones 20 respectively disposed therein, and an upper branch portion 32 for receiving audio waves. The lower forked portion 31 of the audio-wave guide 30 is properly positioned on the level surface 111 with each output conductive cord 142, 143 of the microphones 20 separately connected to the input terminals of the audio-signal amplifying device 140 through the central recess 112. The interior of the upper cover 12 is formed in a shape conforming to that of the audio-wave guide 30, and the upper cover is fixed on the top end of the main body 11 with the forked portion 31 of the audio-wave guide 30 being completely surrounded by the upper cover and being pressed against the level surface 111 of the main body 11 for firm positioning. The branch portion 32 extends out of the opening 121 of the upper cover 12. It shall be appreciated that the connection between the main body 11 and the upper cover 12 as well as between the body 11 and the lower cover 13 can be made through a kind of halved joint by which the protrusions provided at both ends of the main body 11 can be easily engaged with the notches respectively formed in an inner wall of the upper cover 12 and the lower cover 13 so that assembly and disassembly of the housing unit 10 can be quickly made therewith.

As shown in FIGS. 1 and 3, the body contact device 40 is composed of a sound transmission pipe 43 with a diaphragm 41 (for high frequency sounds) on one side, a bell 42 (for low frequency sounds) on the other, and a sound-wave duct 44 in the middle. The device 40 is sleevingly connected to the upper branch portion 32 through the sound-wave duct, of which the lower end is firmly wrapped by the branch portion 32 of the audio-wave guide 30, and the upper part can be turned in unilateral communication with either the diaphragm 41 or the bell 42.

Referring to FIGS. 4 and 5, the wireless radio wave transmitting device 141 includes a wireless radio wave generating circuit 204 formed on the PC board 14, a wireless radio on switch 202 and a wire type antenna 201. The audio wave amplifying device 140 mainly consists of a circuit means which is also formed and arranged on the PC board 14.

Figure 6:
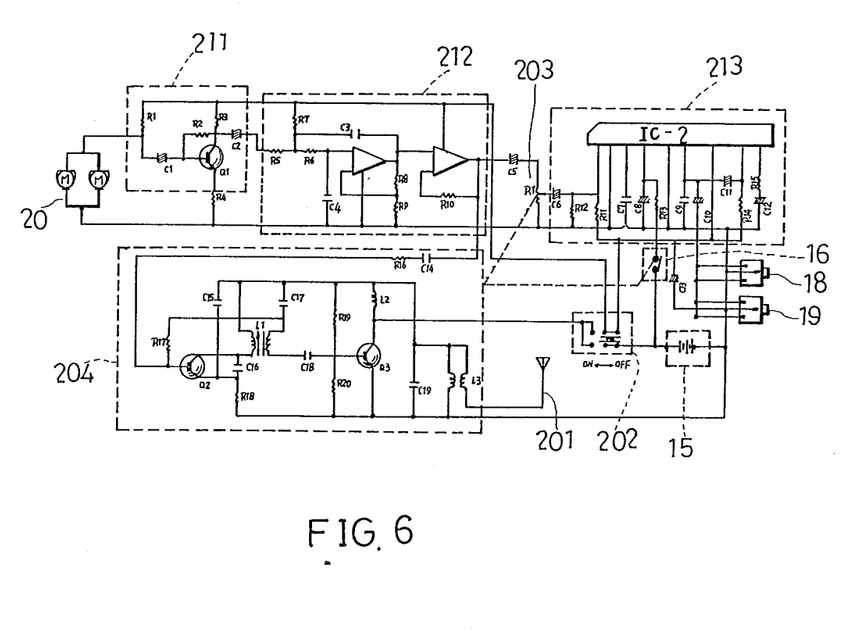
FIG. 6 is an electric circuit diagram embodying the functional block diagram in FIG. 5 for the audio signal amplifying device and the wireless radio wave transmitting device.

FIG. 5 and FIG. 6 which show the functional block diagram and the actual circuit diagram of the audio signal amplifying device and the wireless radio wave transmitting device in the stethoscopic apparatus according to the present invention. The audio wave amplifying device 140 comprises a pre-amplifying device 211, a low pass filtering device 212 which is used to filter those signals of frequencies above 3000 Hertz, a volume control device 203 which is usually a variable resistor for controlling the output of the signal, and a power amplifying circuit means 213. The wireless radio wave transmitting device 141 comprises a wireless radio wave generating circuit means 204 which is usually an oscillation circuit, an antenna 201 and a wireless radio on switch 202. The filtered electric signal is fed into the wireless radio wave generating circuit 204 for oscillation and transmitted through the antenna 201 when the switch 202 is on. The corresponding electric circuit of the audio wave amplifying device 140 and the wireless radio wave transmitting device 141 is best shown in FIG. 6. Since the circuitry is in the area of the conventional art and also self-explanatory for those skilled in the art, the operation of this circuitry will not be detailed hereinbelow for the purpose of simplicity.

The operation of the first assembled preferred embodiment of the electronic stethoscopic apparatus according to this invention is as follows:

Referring to FIGS. 1, 3, 4 and 5, before using the electronic stethoscopic apparatus for auscultation, an earphone 50 for a single user or a speaker 52 for group bed-side teaching or consultation can be connected to the audio-signal amplifying device 140 (FIG. 5) through a signal transmission cord 51 plugged into the earphone/speaker jack 19 of the main body 11. As the situation dictates, the user can select either the diaphragm 41 or the bell 42 along with the audio-wave duct 44 to be placed on the body portion of a patient. Sound detected from the body portion by the body contact device 40 is transmitted through the audio-wave duct 44 and the upper branch 32 of the audio-wave guide 30, and is received by the microphones 20 from which the sound waves are transduced into electrical signals and fed into the audio-signal amplifying device 140. Upon being amplified by the amplifying device 140, audio signals are transmitted to the earphone 50 for auscultation or to the speaker 52 for consultation and/or bed-side teaching through the earphone/speaker jack 19. In addition, if sound recording is needed for establishing the patient's history or for further study, a recorder 60 can also be connected to the audio-signal amplifying device 140 through another electrical conductive cord 61, which is plugged into the recorder jack 18 of the main body 11. Thus, the amplified audio signals from the audio-signal amplifying device 140 can also be fed into the recorder 60 through the recorder jack 18 for sound recording.

If the detected sound is to be transmitted to a remote place such as for the performance of group bedside teaching of auscultation, the user may turn on the wireless radio on switch 202. The wireless radio wave transmitting device 141 is then actuated to transmit the signal through the antenna 201. By the wireless radio wave transmitting device 141, remote auscultation and group bedside teaching of auscultation can be conveniently achieved through a pocketable receiver and an earphone.

It shall be appreciated that since auscultation according to this invention is made through an earphone, it is much more comfortable for the user than the resilient eartips of the conventional stethoscopes. Further than this, with the arrangement of the highly sensitive microphones 20 and the control knob 203 for controlling the amplitude of the audio-wave volume, the detected sound from the body portion of a patient can be optionally amplified and clearly received by the earphone 50 or the speaker 52 for ensuring the correctness and reliability of diagnosis. Moreover, as the detected sound from the body portion of a patient can be recorded, repeated auscultations can be performed when it is necessary, and medical history can be conveniently established for use in the future for bed-side teaching and other purposes. Furthermore, during bed-side teaching or consultation, simultaneous auscultation can be made through the reproduced sound of the speaker 52 electrically connected to the audio-signal amplifying device 140 through the earphone/speaker jack 19 without requiring repeated individual auscultations as is necessary with the conventional stethoscopes.

In addition to the above-noted features, the preferred embodiment of this invention can also be used to convert the detected sound from a patient's body portion into substantial information so as to effectuate visual diagnosis and establish medical data files. In respect of this arrangement, as shown in FIG. 4, an interface of audio control device 80 is electrically connected to the output of the audio-signal amplifying device 140, and an oscillograph 90 and a plotting instrument 100 can be functionally coupled with the output of the audio control device 80 so that audio signals from the patient's body portion can be converted into visual display information for visual diagnosis and/or data processing operation.

Figure 7:
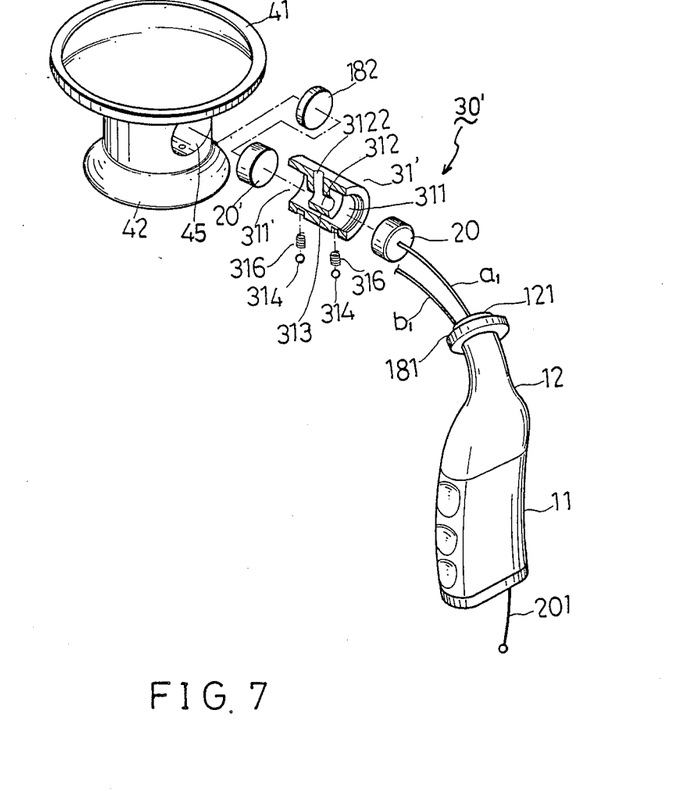
FIG. 7 is an exploded and perspective view of a second preferred embodiment of an electronic stethoscopic apparatus according to the present invention.
Figure 8:
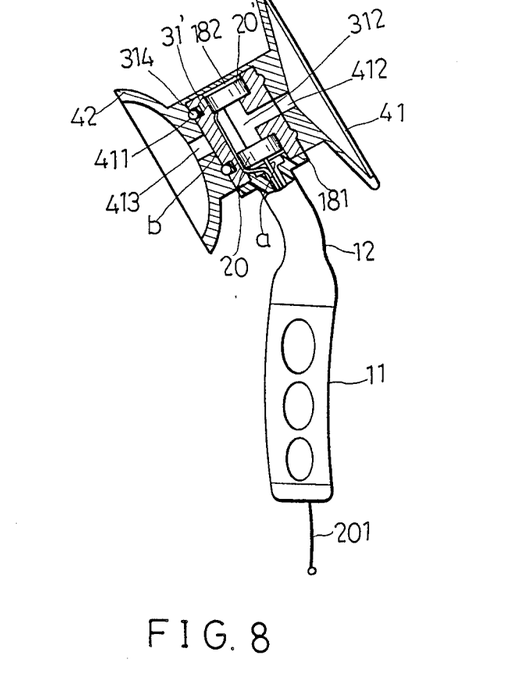
FIG. 8 is a side view showing the assembly, partly in section, of the second preferred embodiment of the stethoscopic apparatus shown in FIG. 2.

Referring to FIGS. 7 and 8 which show the exploded perspective view and partly cut-off sectional view of a second embodiment of the multi-functional electronic stethoscopic apparatus according to the present invention, it is noted that the housing device 11 and most parts of the stethoscopic apparatus in the second embodiment are the same in structure as that in the first embodiment stethoscopic apparatus shown in FIGS. 1 to 3. The audio wave guide 30' includes a lower cover 181 which is connected to a slightly curved upper portion of the casing 12, a cylinder body 31' and an upper cover 182 connected to the upper chamber 311' of the cylinder body 31'. The cylinder body 31' is properly positioned in the round chamber 45 of the chest piece 40 with the vertical portion 3122 of the three-way opening 312 aligned with the opposing communication opening 412 or 413, and the steel balls 314 biased by springs 316 respectively located in the orifices 411 so as to keep the cylinder body 31' in position in the round chamber 45 of the chest piece 40. The conductive cords a and b of the microphones 20, 20', which are separately located in the lower and upper chambers 311, 311', are connected to the audio wave amplifying device and the wire transmission line through the upper opening 121 of the upper casing 12 with the cord b1 passing through the penetrating hole 313 of the cylinder body 31'. It can be particularly noted that the audio wave guiding means 30' is not like that shown in FIGS. 1 to 3 in a Y-shaped configuration. The audio signal amplifying device 140 and the wireless radio wave transmitting device 141 are incorporated in the electronic stethoscopic apparatus of the second embodiment shown in FIGS. 7 and 8. The operation of the second embodiment electronic stethoscopic apparatus is exactly the same as that of the stethoscopic apparatus shown in the first embodiment.

While a preferred embodiment has been illustrated and described, it will be apparent that many changes may be made in the general construction and arrangement of the invention without departing from the spirit and scope thereof, and it is therefore desired that the invention be not limited to the exact disclosure but only to the extent of the appending claims.

What is claimed is:

1. An electronic stethoscopic apparatus comprising:
   a housing means adapted for hand gripping and operational control;
   an audio-signal amplifying means having input/output terminals provided therein installed in said housing means for amplifying and outputting audio signals therefrom;
   power supply means replaceably installed in said housing means and electrically connected to said audio-signal amplifying means for providing power thereto;

an audio-wave guiding means disposed on said housing means for receiving and transmitting sound waves;

transducing means having output terminals provided thereto disposed in said audio-wave guiding means and electrically connected to said audio-signal amplifying means for receiving said sound waves and converting same into electrical audio signals to be fed into said audio-signal amplifying means; and a body contact means composed of a sound transmission pipe with a diaphram on one side, a bell on another, and a sound-wave duct in a middle portion thereof, sleevingly connected to said audio-wave guiding means for detecting sound waves from a body portion of a patient.

2. An electronic stethoscopic apparatus according to claim 1 wherein said housing means comprises:

a main body formed in an elongated shape and having a level surface with a central recess formed therein said audio-wave guiding means being positioned on said level surface:

a first cover detachably connected to one end of the main body;

a recorder jack and an earphone/speaker jack in the main body and electrically connected to said audio-signal amplifying means, said audio-signal amplifying means being installed in the main body;

a control knob provided on the main body and electrically connected to said audio-signal amplifying means for controlling the magnitude of output audio signals therefrom; and a second cover having an inner section formed in a shape conforming to that of said audio-wave guiding means connected to the main body for wrappingly pressing a portion of said audio-wave guiding means against said level surface with another portion of said audio-wave guiding means extending out of the second cover and being sleevingly connected with the sound-wave duct of said body contact means.

3. An electronic stethoscopic apparatus according to claim 1 further comprising a wireless radio wave transmitting means to receive said audio signals from said audio signal amplifying means and generating an output wireless radio signal.

4. An electronic stethoscopic apparatus according to claim 3 wherein said wireless radio wave transmitting means comprises a wireless radio wave generating circuit means and an antenna connected to said circuit means.

5. An electronic stethoscopic apparatus comprising:

a body contact device;

an audio wave guiding means installed in said body contact device for receiving audio waves therein;

a pair of transducing means disposed in said body contact device for converting audio waves into electrical signals and transferring the signals therefrom;

a housing means connected to said audio wave guiding means;

an audio wave amplifying device disposed in said housing means for amplifying said electrical signals;

a wireless radio wave transmitting device installed in said housing means for transforming said electrical signal into wireless radio wave signals;

a power supply means provided in said housing means for supplying power to said audio wave amplifying device and said wireless radio wave transmitting device; and switching on/off switches for said power supply means and said wireless radio wave transmitting device.

6. An electronic stethoscopic apparatus according to claim 1 wherein said audio signal amplifying means further comprises a pre-amplifying device, a low pass filtering device for filtering out high frequency ambient noise, and power amplifying circuit means.

* * * * *